(12) United States Patent
Walters et al.

(10) Patent No.: US 8,979,818 B2
(45) Date of Patent: Mar. 17, 2015

(54) METHOD AND APPARATUS FOR THE DELIVERY OF POLYNUCLEOTIDE VACCINES TO MAMMALIAN SKIN

(75) Inventors: Richard E. Walters, Severna Park, MD (US); Robert J. Walters, legal representative, Severna Park, MD (US); Derin C. Walters, Austin, TX (US); Alan D. King, Highland, MD (US); Anna-Karin Roos, Spånga (SE)

(73) Assignee: Cellectis, Paris (FR)

( * ) Notice: Subject to any disclaimer, the term of this patent is extended or adjusted under 35 U.S.C. 154(b) by 204 days.

(21) Appl. No.: 13/065,135

(22) Filed: Mar. 15, 2011

(65) Prior Publication Data
US 2011/0166501 A1    Jul. 7, 2011

Related U.S. Application Data

(63) Continuation of application No. 12/451,536, filed as application No. PCT/US2008/006442 on May 20, 2008, now abandoned.

(60) Provisional application No. 60/924,568, filed on May 21, 2007.

(51) Int. Cl.
| | |
|---|---|
| *A61N 1/30* | (2006.01) |
| *A61M 31/00* | (2006.01) |
| *A61M 35/00* | (2006.01) |
| *A61N 1/32* | (2006.01) |
| *A61K 39/12* | (2006.01) |
| *C07K 14/005* | (2006.01) |
| *A61K 39/00* | (2006.01) |

(Continued)

(52) U.S. Cl.
CPC .............. *A61N 1/327* (2013.01); *A61K 39/12* (2013.01); *C07K 14/005* (2013.01); *A61K 2039/53* (2013.01); *A61K 2039/54* (2013.01); *A61N 1/306* (2013.01); *C12N 2770/24122* (2013.01)

USPC .............. 604/501; 604/19; 604/20; 604/21; 604/48; 604/289

(58) Field of Classification Search
USPC .................. 604/19–21, 48, 289, 500–501
See application file for complete search history.

(56) References Cited

U.S. PATENT DOCUMENTS 6,520,950 B1 *  2/2003  Hofmann et al. .............. 604/503
6,603,998 B1 *  8/2003  King et al. ....................... 604/20

(Continued)

*Primary Examiner* — Emily Schmidt
*Assistant Examiner* — Lauren M Peng
(74) *Attorney, Agent, or Firm* — Marvin S. Towsend

(57) ABSTRACT

An object of the invention is to provide a method and apparatus for the delivery of polynucleotide vaccines into mammalian skin cells to increase T cell response and to reduce pain and discomfort due to long electric waveform application and due to muscle contractions. The method for the delivery of polynucleotide vaccines into mammalian skin cells includes the steps of: (a.) administering a polynucleotide vaccine into the skin at an administration site, (b.) applying a needle electrode to the skin in the vicinity to the administration site, and (c.) applying a sequence of at least three single, operator-controlled, independently programmed, narrow interval electrical waveforms, which have pulse intervals that are less than 100 milliseconds, to deliver the polynucleotide vaccine into the skin cells by electroporation. The sequence of at least three waveforms has one, two, or three of the following characteristics (1) at least two of the at least three waveforms differ from each other in waveform amplitude, (2) at least two of the at least three waveforms differ from each other in waveform width, and (3) a first waveform interval for a first set of two of the at least three waveforms is different from a second waveform interval for a second set of two of the at least three waveforms.

13 Claims, 3 Drawing Sheets

(56) References Cited

U.S. PATENT DOCUMENTS

| | | | |
|---|---|---|---|
| 6,713,291 B2 * | 3/2004 | King et al. | 435/173.6 |
| 6,947,791 B2 * | 9/2005 | Zhang et al. | 604/20 |
| 6,972,013 B1 * | 12/2005 | Zhang et al. | 604/501 |
| 2002/0061589 A1 * | 5/2002 | King et al. | 435/446 |
| 2004/0203124 A1 * | 10/2004 | King et al. | 435/173.6 |
| 2011/0166501 A1 * | 7/2011 | Walters et al. | 604/20 |

\* cited by examiner

US 8,979,818 B2

METHOD AND APPARATUS FOR THE DELIVERY OF POLYNUCLEOTIDE VACCINES TO MAMMALIAN SKIN

CROSS-REFERENCE TO RELATED APPLICATION

This application claims priority based upon U.S. patent application Ser. No. 12/451,536, filed Feb. 23, 2010 now abandoned, having an I. A. Filing Date of May 20, 2008 and U.S. Provisional Application Ser. No. 60/924,568, filed 21 May 2007.

TECHNICAL FIELD

The present invention relates generally to methods and apparatus for the delivery of polynucleotide vaccines into mammalian skin cells. More specifically, the present invention provides methods and apparatus for the delivery of polynucleotide vaccines into mammalian skin cells using electrical waveforms and electroporation.

BACKGROUND ART

For purposes of the present disclosure, the term "pulse interval" means the time from the beginning of one pulse to the beginning of the next pulse.

The following publications are discussed hereinbelow:
U.S. Pat. No. 6,010,613;
U.S. Pat. No. 6,603,998;
U.S. Pat. No. 6,713,291;
"Enhancement of Cellular Immune Response to a Prostate Cancer DNA Vaccine by Intradermal Electroporation", by Roos et al, Molecular Therapy, Vol. 13, No. 2, February 2006, pages 320-327 (referred to herein as Roos et al);
"The effect of pulse repetition frequency on the uptake into electropermeabilized cells in vitro with possible applications in electrochemotherapy", by Pucihar et al, Bioelectrochemistry 57 (2002) pages 167-172 (referred to herein as Pucihar et al).
Vernhes M C, Cabanes P A, Tessie J. Chinease hamster ovary cells sensitivity to localized electrical stress. Bioelectrochemistry and Bioenergetics. 1999, 48:17-25;
Daskalov I, Mudrov N, Peycheva E. Exploring new instrumentation. Parameters for electrochemotherapy. Attacking tumors with bursts of biphasic pulses instead of single pulses. 1999, IEEE Eng. Med. Biol 62-66; Chang D C, Cell poration and cell fusion using an oscillating electric field. 1989 Biophys J. 56:641-652; and
Tekle E, Astumian R D, Chock P B. Electroporation by using bipolar oscillating electric field: An improved method for DNA transfection of NIH 3T3 cells. 1991 Proc. Natl. Acad. Sci. 88:4230-4234.

U.S. Pat. No. 6,010,613, incorporated herein by reference, discloses using electroporation with wide interval electrical waveforms, such as provided by PA-4000 System (referred to herein as PulseAgile) of Cyto Pulse, Inc., 810 Cromwell Park Drive, Suite T, Glen Burnie, Md. 21061. More specifically, U.S. Pat. No. 6,010,613 discloses applying a sequence of at least three single, operator-controlled, independently programmed, DC electrical pulses, to a material, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses.

For purposes of the discussions and disclosures herein, the above-mentioned applying a sequence of at least three single, operator-controlled, independently programmed, DC electrical pulses, to a material, with the characteristics (1), (2), and (3) set forth is referred to herein as "PulseAgile".

The specification disclosed in U.S. Pat. No. 6,010,613 and the documentation connected with the PulseAgile system provide that the pulse interval is equal to or greater than 0.1 seconds, which is 100 milliseconds. Hereinafter, the PulseAgile generated electrical waveforms which have pulse intervals which are equal to or greater than 100 milliseconds are referred to as "wide interval PulseAgile electrical waveforms" or "slow PulseAgile electrical waveforms".

In U.S. Pat. No. 6,010,613, there is no specific evidence presented that administered vaccines have either successful genetic expression of the vaccine or provide improved T-cell response involving improved secretion of good protein resulting from successful genetic expression of the vaccine.

Both U.S. Pat. No. 6,603,998 and U.S. Pat. No. 6,713,291, both incorporated herein by reference, disclose the delivery of polynucleotide vaccines to biological cells using the wide interval PulseAgile electrical waveforms or slow PulseAgile electrical waveforms.

Roos et al disclose the use of the wide interval PulseAgile electrical waveforms or slow PulseAgile electrical waveforms to deliver a polynucleotide vaccine into mammalian skin cells. It is also disclosed by Roos et al that successful genetic expression of the polynucleotide vaccine is demonstrated by detection of a genetic marker which expresses luciferase protein. In addition, Roos et al disclose that with the use of the wide interval PulseAgile electrical waveforms or the slow PulseAgile electrical waveforms to deliver a polynucleotide vaccine into mammalian skin cells, there is improved T-cell response involving improved secretion of good protein resulting from successful genetic expression of the polynucleotide vaccine. In Roos et al, T-cell response is represented by PSA-specific IFN(gamma)-producing $CD8^+$ T cells.

Aside from the beneficial results disclosed in the Roos et al publication, there are two undesirable results observed by using the slow PulseAgile electrical waveforms. The first undesirable result is that each slow PulseAgile electrical waveform administration protocol took approximately 3.5 seconds. Since administration employing the use of needles penetrating into mammalian skin causes discomfort or pain, for such 3.5 second administration protocol, the mammal would have to endure the discomfort or pain for approximately 3.5 seconds.

The second undesirable result disclosed in Roos et al is that each slow PulseAgile electrical waveform causes a perceptible muscle contraction. The muscle contraction itself can also cause discomfort or pain. Normally, for an administration of a polynucleotide vaccine, plural pulsed waveforms would be applied to a mammal. Therefore, plural muscle contractions, with plural additional muscle discomfort or pain, would take place with such slow PulseAgile electrical waveforms.

Pucihar et al disclose that, before their publication date in 2002, electrical pulses have been used in combination with chemotherapeutic agents to treat cancerous cells. The earlier electrical pulses have had a frequency of 1 Hz, whereby each pulse produced a related tetanic contraction (muscle contraction). It is noted that 1 Hz translates to 1000 milliseconds per cycle. The discussed electrical pulse protocols are all pulse sequences that have pulses of uniform pulse amplitude, uniform pulse width, and uniform pulse interval. The chemotherapeutic agents include small nonpermeant hydrophilic molecules. The disclosures of the research conducted by Pucihar et al relate to in vitro (not in vivo) experiments with cancerous cell being treated with Lucifer Yellow, which is a small nonpermeant hydrophilic molecule. The disclosures of the research conducted by Pucihar et al explore various pulse repetition frequencies in order to exceed the frequency of tetanic contraction (so that successive muscle contractions fuse into smooth motion). There is a statement in Pucihar et al that with a frequency of excitation of 40 Hz or faster, successive muscle contractions fuse into smooth motion. The 40 Hz pulse frequency employs pulses of uniform pulse amplitude, uniform pulse width, and uniform pulse interval. It is noted that 40 Hz translates to 25 milliseconds per cycle.

Vernhes et al disclose that viability and permeability of CHO cells electroporated in vitro were high over an electroporation pulse frequency range of 0.5 to 100 HZ.

Daskalov et al disclose that eight bipolar pulses delivered to tumor cells in vivo produced a similar response to electrochemotherapy when delivered at 1 HZ and 1 kHZ.

Chang discloses that high frequency sinusoidal waveforms delivered as short pulses efficiently electroporated COS-M-6 cells in vitro.

Tekle et al disclose that unipolar or bipolar rectangular wave pulses delivered at frequencies ranging from 60 kHZ to 1 MHZ efficiently transfected NIH 3T3 cells in vitro.

There is no disclosure in any of Pucihar, Vernhes et al, Daskalov et al, Chang, or Tekle et al which states any relationship to polynucleotide vaccination, to successful genetic expression of a polynucleotide vaccine, or to improved T-cell response involving improved secretion of a desired protein resulting from successful genetic expression of the polynucleotide vaccine.

In view of the above, it would be desirable to provide a method and apparatus for the delivery of polynucleotide vaccine into mammalian skin cells which takes less than 3.5 seconds to administer the polynucleotide vaccine.

In addition, it would be desirable to provide a method and apparatus for the delivery of polynucleotide vaccines into mammalian skin cells which applies plural PulseAgile electrical waveforms to the mammalian skin and only causes one muscle contraction for the plural applied electrical waveforms.

Administration of a polynucleotide vaccine, to be successful, must give evidence of successful genetic expression of the administered polynucleotide vaccine. Moreover, to be successful, the genetic expression of the administered polynucleotide must give evidence of providing a desired protein which results from the successful genetic expression of the polynucleotide vaccine.

Thus, while the foregoing body of prior art indicates it to be well known to use electroporation apparatuses, the prior art described above does not teach or suggest a method and apparatus for the delivery of polynucleotide vaccines into mammalian skin cells which has the following combination of desirable features: (1) provides a method and apparatus for the delivery of polynucleotide vaccine into mammalian skin cells which takes less than 3.5 seconds to administer the polynucleotide vaccine; (2) applies plural PulseAgile electrical waveforms to the mammalian skin and only causes one muscle contraction for the plural applied electrical waveforms; (3) gives evidence of successful genetic expression of the administered polynucleotide vaccine; and (4) gives evidence of providing a desired protein which results from the successful genetic expression of the polynucleotide vaccine.

The foregoing desired characteristics are provided by the unique method and apparatus for the delivery of polynucleotide vaccines into mammalian skin cells of the present invention as will be made apparent from the following description thereof. Other advantages of the present invention over the prior art also will be rendered evident.

The foregoing desired characteristics are provided by the unique method and apparatus for the delivery of polynucleotide vaccines into mammalian skin cells of the present invention as will be made apparent from the following description thereof. Other advantages of the present invention over the prior art also will be rendered evident.

DISCLOSURE OF INVENTION

In accordance with one aspect of the invention, a method for the delivery of polynucleotide vaccines into mammalian skin cells includes the steps of:

(a.) administering a polynucleotide vaccine into the skin at an administration site, (b.) applying a needle electrode to the skin in the vicinity to the administration site, and (c.) applying a sequence of at least three single, operator-controlled, independently programmed, narrow interval electrical waveforms, which have pulse intervals that are less than 100 milliseconds, to deliver the polynucleotide vaccine into the skin cells by electroporation. The sequence of at least three waveforms has one, two, or three of the following characteristics (1) at least two of the at least three waveforms differ from each other in waveform amplitude, (2) at least two of the at least three waveforms differ from each other in waveform width, and (3) a first waveform interval for a first set of two of the at least three waveforms is different from a second waveform interval for a second set of two of the at least three waveforms.

The sequence of at least three single, operator-controlled, independently programmed, narrow interval electrical waveforms, which have pulse intervals that are less than 100 milliseconds are referred to herein as "fast PulseAgile electrical waveforms" or as "narrow interval PulseAgile electrical waveforms".

Preferably, the narrow interval electrical waveforms have a pulse interval of less than a few milliseconds.

With one embodiment of the method of the invention, step (a.) and step (b.) are carried out sequentially. For example, a DNA vaccine is first injected into the skin to form a bleb. Then, a needle electrode is placed into the skin straddling the bleb. In this respect, the "Derma Vax" system can be employed.

With another embodiment of the method of the invention, step (a.) and step (b.) are carried out simultaneously using an electrode that is pre-coated with the polynucleotide vaccine. In this respect, "Easy Vax" system can be employed.

In accordance with another aspect of the invention, an apparatus is provided for the delivery of polynucleotide vaccines into mammalian skin cells which includes a narrow interval electrical waveform generator, which is capable of applying a sequence of at least three single, operator-controlled, independently programmed, narrow interval electrical waveforms, which have pulse intervals that are less than 100 milliseconds; and which includes an electrode which is adapted to contact the skin into which a polynucleotide vaccine has been applied.

The sequence of at least three waveforms has one, two, or three of the following characteristics (1) at least two of the at least three waveforms differ from each other in waveform amplitude, (2) at least two of the at least three waveforms differ from each other in waveform width, and (3) a first waveform interval for a first set of two of the at least three waveforms is different from a second waveform interval for a second set of two of the at least three waveforms, and an electrode is connected to the narrow interval electrical waveform generator.

With one embodiment of the apparatus of the invention, the polynucleotide vaccine is applied to the skin prior to contacting the skin with the electrode. This can be accomplished by using a hypodermic needle.

With another embodiment of the apparatus of the invention, the polynucleotide vaccine is pre-coated on the electrode and is applied to the skin at the same time the electrode is contacted with the skin.

The apparatus that provides fast PulseAgile electrical waveforms or narrow interval PulseAgile electrical waveforms and that employs any suitable electrode for application to mammalian skin is made by Cyto Pulse, Inc., 810 Cromwell Park Drive, Suite T, Glen Burnie, Md. 21061, and is known by the name "Derma Vax".

More information about the Cyto Pulse, Inc. "Derma Vax" system is in the following publication: a Data Sheet entitled "Derma Vax™ Clinical Evaluation Intra-dermal System", which available to the public on the Internet at the following URL address—www.cytopulse.com/dna_vaccine.shtml, followed by a click on the link entitled "Derma Vax Data Sheet (99 Kb)". The Data Sheet itself is located at the following URL address—http://www.cytopulse.com/pdf/Datasheet%20Derma%20Vax.pdf.

The apparatus that provides fast PulseAgile electrical waveforms or narrow interval PulseAgile electrical waveforms and that employs a pre-coated electrode suitable for application to mammalian skin is also made by Cyto Pulse, Inc. and is known by the name "Easy Vax".

The apparatus that provides fast PulseAgile electrical waveforms or narrow interval PulseAgile electrical waveforms is also made by Cyto Pulse, Inc. and is known by the name "CCEP-40 Waveform Generator". As stated above, specifications for the "CCEP-40 Waveform Generator" are provided in the Data Sheet entitled "Derma Vax™ Clinical Evaluation Intra-dermal System" mentioned above.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining some implementations of the principles of the invention in greater detail below, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved method and apparatus for the delivery of polynucleotide vaccines into mammalian skin cells which takes less than 3.5 seconds to administer the polynucleotide vaccine.

Still another object of the present invention is to provide a new and improved method and apparatus for the delivery of polynucleotide vaccines into mammalian skin cells that applies plural PulseAgile electrical waveforms to the mammalian skin and only causes one muscle contraction for the plural applied electrical waveforms.

Yet another object of the present invention is to provide a new and improved method and apparatus for the delivery of polynucleotide vaccines into mammalian skin cells which gives evidence of successful genetic expression of the administered polynucleotide vaccine.

Even another object of the present invention is to provide a new and improved method and apparatus for the delivery of polynucleotide vaccines into mammalian skin cells that gives evidence of providing a desired protein which results from the successful genetic expression of the polynucleotide vaccine.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein.

MODES FOR CARRYING OUT THE INVENTION

Figure 1:
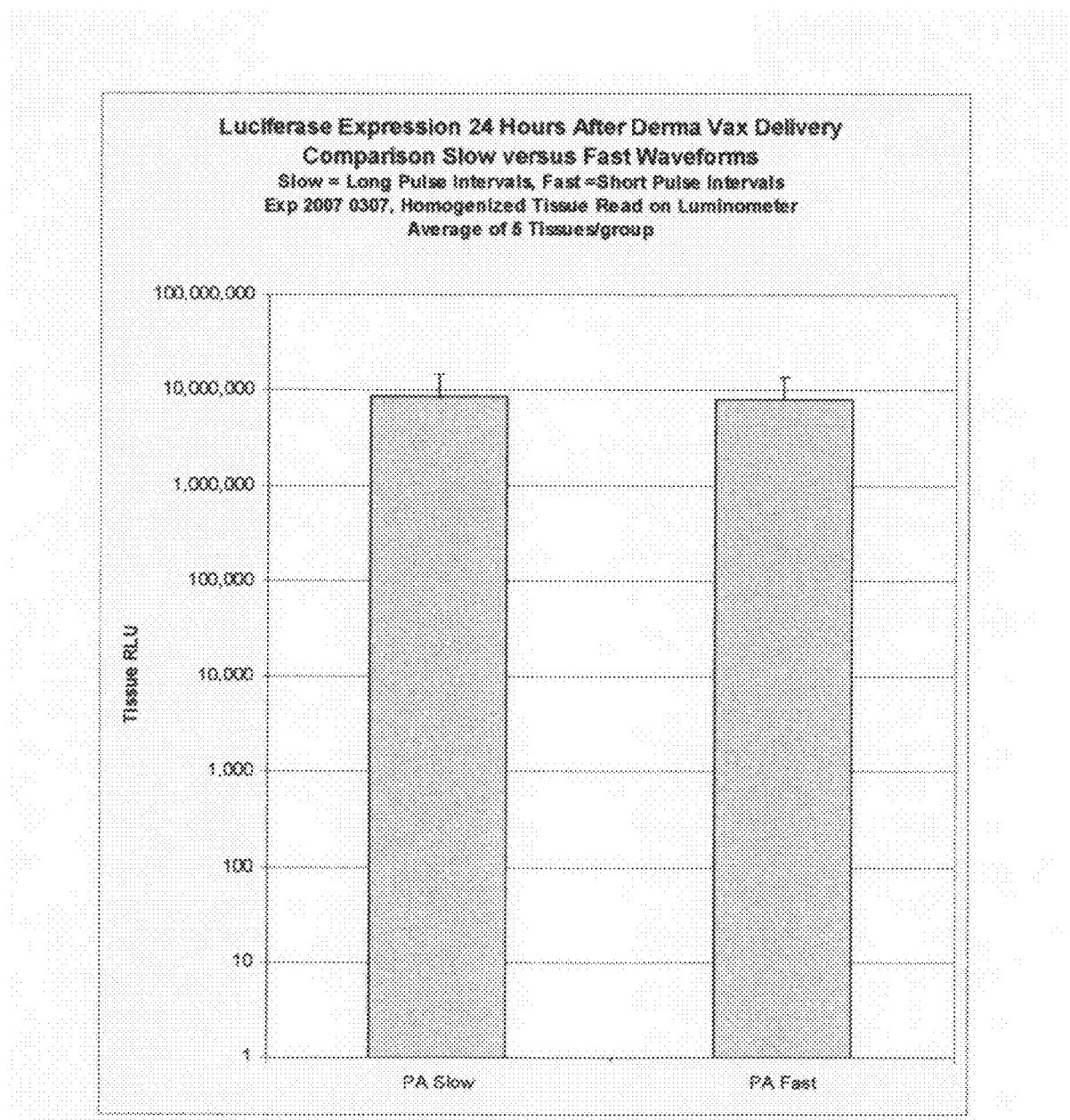
FIG. 1 is a graph illustrating a comparison of luciferase expression resulting from the application of fast PulseAgile electrical waveforms versus the application of slow PulseAgile electrical waveforms for delivery of luciferase plasmid with electroporation using "Derma Vax" equipment.

A method and apparatus are provided for the delivery of polynucleotide vaccines into mammalian skin cells, and with reference to the drawings, said method and apparatus are described below.

Specifications for "Derma Vax" and "CCEP-40 Waveform Generator" are as follows:
DERMA VAX Specifications
Operation
  Mode 1—Vaccine Delivery by Trained Health Professional
    Touch Screen
      Opening Screen for parameter entry
        Patient ID entry
        Vaccine ID entry
        Electrode ID entry Vaccination Screen
  SKIN—measure skin resistance every second and display
  READY—turn on high voltage power supply
  START—start pulsing
  DONE—vaccination completed
Mode 2—Setup by Trained IT Specialist
Pulse parameters
Download data files
Delivery Electrode
  Vaccine Delivery Volume
  2 blebs×25 µl each IDA-4-6
  2 blebs×50 µl each IDA-6-6
  Delivery target—skin/dermis
  Electrode
  Handle—Reusable with alcohol cleaning
  Tip—
    Sterile
    Single packaged
    Disposable

|  | IDA-4-4 | IDA-4-6 | IDA-6-6 |
|---|---|---|---|
| Row spacing | 4 mm | 4 mm | 6 mm |
| Needles/row | 4 | 6 | 6 |
| Needle spacing | 1.5 mm | 1.5 mm | 1.5 mm |
| Needle diameter | 0.3 mm | 0.3 mm | 0.3 mm |
| Needle length | 2 mm | 3 mm | 3 mm |
| V/d maximum | 2500 v/cm | 2500 v/cm | 1667 v/cm |

CCEP-40 Waveform Generator
Pulsing
  Skin resistance pulsing—4 µs at 5 volts every second
  Pulse Protocol Parameters

| Parameters in a Group | |
|---|---|
| Pulse Width | 50 µs to 1 ms 50 to 1000 volts |
|  | 50 µs to 10 ms 50 to 300 volts |
| Pulse current trip | 26 amps |
| Load Range | 15 to 1500 ohms |
| Number of pulses | 1 to 10 |
| Maximum Duty Cycle | 50% |
| Interval | 200 µs to 1 sec (pulse start to pulse start) |
| Number of Groups | 3 |

Pulse Measurement
  Internal Digitizer
  Levels 12 bit
  Samples Pulse width/8 minimum 100 µs
Data stored internally and on external USB Key
Data Types
  Raw data: DV<Date>.xml
  Log Data DV<Date>.txt
  CSV Data DV<Date>.csv
All data automatically stored in internal memory and may be downloaded to an external USB Key
Maximum Data Logs stored and retrievable from internal flash memory>20,000
Front Panel
  Computer
  Operating System Windows™ Mobile 6.0
  Interface Touch screen
  Line/Mains Switch with illumination
  Emergency Stop Button (resets computer to ready state)
  Touch Screen
  USB Ports 2
  Electrode connector Fischer Series 4032
Back Panel
  Power Entry IEC 320
  Ethernet RJ45
Electrical and Mechanical

| CCEP-40A Cabinet with handle | 32 mm w × 20 mm h × 40 mm l |
|---|---|
|  | 12.6 in w × 7.9 in h × 15.7 in l |
| Weight | 25 pounds, 11.3 kg |
| Operating temperature | 10 to 40° C. |
| Mains Voltage | 100 to 250 vac |
| Fuse | 5 A slo blo, 5 mm × 20 mm |
| Power reserve | >5 minutes after power fail |

Experiments for carrying out the method of the invention employing apparatus of the invention for the delivery of polynucleotide vaccines into mammalian skin cells are set forth below.

Experiment 1

Purpose and Scope

The purpose of this experiment is to compare fast PulseAgile electrical waveforms (using the Cyto Pulse "Derma Vax" system) versus slow PulseAgile electrical waveforms (using the Cyto Pulse PA-4000 system). The new Derma Vax system can deliver pulses more rapidly than the PA-4000.
Background
Dr. Anna-Karin Roos published at least two waveforms that induced good luciferase expression in the skin of mice. The system used was the PA-4000, and slow PulseAgile electrical waveforms were employed. New capabilities have been engineered into the Derma Vax system which employs the "CCEP-40 Waveform Generator". One significant difference is that the Derma Vax system can deliver pulses with shorter pulse intervals. That is, with the "Derma Vax" system, pulse intervals of less than 100 milliseconds can be provided. This experiment will evaluate the effect on in vivo luciferase expression using fast PulseAgile electrical waveforms.
Approach
Plasmid used: gWizLuciferase from Aldeveron at 5 mg/ml diluted to 0.5 mg/ml in sterile PBS.
System: Derma Vax #F2LQ2608851
Electrode: Intradermal Array (4 mm gap, 6 needles per row, 2 rows) parallel row electrode.
Injections: Mice were restrained using a 50 ml conical tube modified with breathing holes. The mouse was inserted head first into the tube. The tail was draped over my left index finger. A small patch of hair was removed on the base of the tail using small scissors. Using a 27 gauge, 0.5 in needle on a tuberculin syringe, a 20 microliter intradermal injection was made on the right side of the base of the tail and sacrum. The site was marked using a Sharpee pen. The rows of needles were inserted around the injection site with the electrode gap oriented left to right and therefore the rows were aligned cranially and caudally. The selected electroporation protocol was initiated and the needles removed. This process was repeated on the left side of the sacrum.
Groups (shown as cages in results). All times are shown in milliseconds

| Protocols | Cage 1 | Cage 2 |
|---|---|---|
| V/d 1 | 1125 | 1125 |
| V1 | 450 | 450 |
| PW 1 | 0.05 | 0.05 |
| #1 | 1 | 1 |
| PI1 | 300 | 0.2 |
| V/d2 | 1125 | 1125 |

-continued

| Protocols | Cage 1 | Cage 2 |
|---|---|---|
| V2 | 450 | 450 |
| PW 2 | 0.05 | 0.05 |
| # 2 | 1 | 1 |
| PI2 | 500 | 100 |
| V/d 3 | 275 | 275 |
| V3 | 110 | 110 |
| PW 3 | 10 | 10 |
| #3 | 8 | 8 |
| PI 3 | 300 | 20 |

Mice were returned to their cages.

After 18-24 hours, the mice were euthanized using $CO_2$ inhalation. Tissue from each of the two sites was incised using a 6 mm punch biopsy. Subcutaneous tissue was removed using scissors and the skin with subcutaneous tissue was added to 1 ml of lysis buffer. The sample was kept on ice until the assay.

Tissues were homogenized using a model IKA tissue homogenizer. A 50 microliter sample of the 1 ml homogenate was added to a white assay plate. Standards were made by diluting a know amount of luciferase with lysis buffer using a three fold dilution series. 50 microliter reagent A of the luciferase assay kit was added to each well. The plate was added to the 96 well luminometer. 50 microliter of reagent B was added and the resulting light was measured over one second.

Data was exported to an Excell spreadsheet for data analysis.

Reference is made to FIG. 1 in the drawings for a graphical representation of the results. There is a statistical equivalence of genetic expression between fast and slow electrical waveform protocols.

Results

|  | Cage 1<br>PA Slow | ng/site<br>Cage 2<br>PA Fast |
|---|---|---|
|  | 22 | 43 |
|  | 464 | 510 |
|  | 486 | 283 |
|  | 180 | 267 |
|  | 197 | 168 |
| Mean | 270 | 254 |
| SD | 200 | 172 |
| CV | 74 | 68 |

It is a surprising and unexpected result that electroporation of a polynucleotide vaccine into mammalian skin cells along with successful gene expression can occur with fast PulseAgile electrical waveforms having a pulse interval of less than 100 milliseconds.

It is an even greater surprising and unexpected result that electroporation of a polynucleotide vaccine into mammalian skin cells, along with successful gene expression, can occur with fast PulseAgile electrical waveforms having a pulse interval of a few milliseconds. Conventionally, it would be expected that the time constant of pulse intervals of only a few milliseconds would be too low for successful electroporation.

Experiment 2

Purpose and Scope

The purpose of this experiment is to compare T cell responses induced by DNA immunization using fast PulseAgile electrical waveforms (using the Cyto Pulse "Derma Vax" system) versus slow PulseAgile electrical waveforms (using the Cyto Pulse PA-4000 system). The new Derma Vax system can deliver pulses more rapidly than the PA-4000. More specifically, the purpose of this study is to compare T cell responses induced by DNA immunization using Pulse Agile Derma Vax delivery with Dengue 1 plasmids expressing prM-E and NS1-IS3.

Background

Dr. Anna-Karin Roos published at least two waveforms that induced good luciferase expression in the skin of mice. The system used was the PA-4000, and slow PulseAgile electrical waveforms were employed. New capabilities have been engineered into the Derma Vax system which employs the "CCEP-40 Waveform Generator". One significant difference is that the Derma Vax system can deliver pulses with shorter pulse intervals. That is, with the "Derma Vax" system, pulse intervals of less than 100 milliseconds can be provided. This experiment will evaluate the effect on in vivo T cell responses using fast PulseAgile electrical waveforms.

Approach

Plasmid used: Dengue 1 prM-E and Dengue 1 NS1-NS3 at 5 mg/ml each diluted to 0.5 mg/ml in the same sterile PBS.

System: Derma Vax #07-0215DV

Electrode: Intradermal Array (4 mm gap, 6 needles per row, 2 rows) parallel row electrode.

Injections: Mice were restrained using a 50 ml conical tube modified with breathing holes. The mouse was inserted head first into the tube. The tail was draped over my left index finger. A small patch of hair was removed on the base of the tail using small scissors. Using a 27 gauge, 0.5 in needle on a tuberculin syringe, a 20 µl intradermal injection was made on the right side of the base of the tail and sacrum. The rows of needles were inserted around the injection site with the electrode gap oriented left to right and therefore the rows were aligned cranially and caudally. The selected electroporation protocol was initiated and the needles removed. This process was repeated on the left side of the sacrum Groups (shown as cages in results). All times are shown in milliseconds

| Protocols | Group P | Group O | Control |
|---|---|---|---|
| V/d 1 | 1125 | 1125 | 0 |
| V1 | 450 | 450 | 0 |
| PW 1 | 0.05 | 0.05 | 0 |
| # 1 | 1 | 1 | 0 |
| PI 1 | 0.2 | 300 | 0 |
| V/d 2 | 1125 | 1125 |  |
| V2 | 450 | 450 |  |
| PW 2 | 0.05 | 0.05 |  |
| # 2 | 1 | 1 |  |
| PI 2 | 30 | 300 |  |
| V/d 3 | 275 | 275 |  |
| 3 | 110 | 110 |  |
| PW 3 | 10 | 10 |  |
| # 3 | 8 | 8 |  |
| PI 3 | 20 | 100 |  |

Mice were returned to their cages.

At 2 weeks after immunization, mice were euthanized using $CO_2$ inhalation and the spleens were collected for intracellular cytokine assay.

Results

Results show below are percent of CD8 positive cells that are gamma interferon positive.

Results are shown with background from un-immunized animals subtracted.

|      | Fast (Group P) | Slow (Group O) |
|------|----------------|----------------|
|      | 6.42           | 4.03           |
|      | 5.38           | 6.11           |
|      | 4.35           | 3.36           |
|      | 4.28           | 2.75           |
|      | 2.06           | 2.16           |
| Mean | 4.50           | 3.68           |
| SD   | 1.62           | 1.53           |

Figure 2:
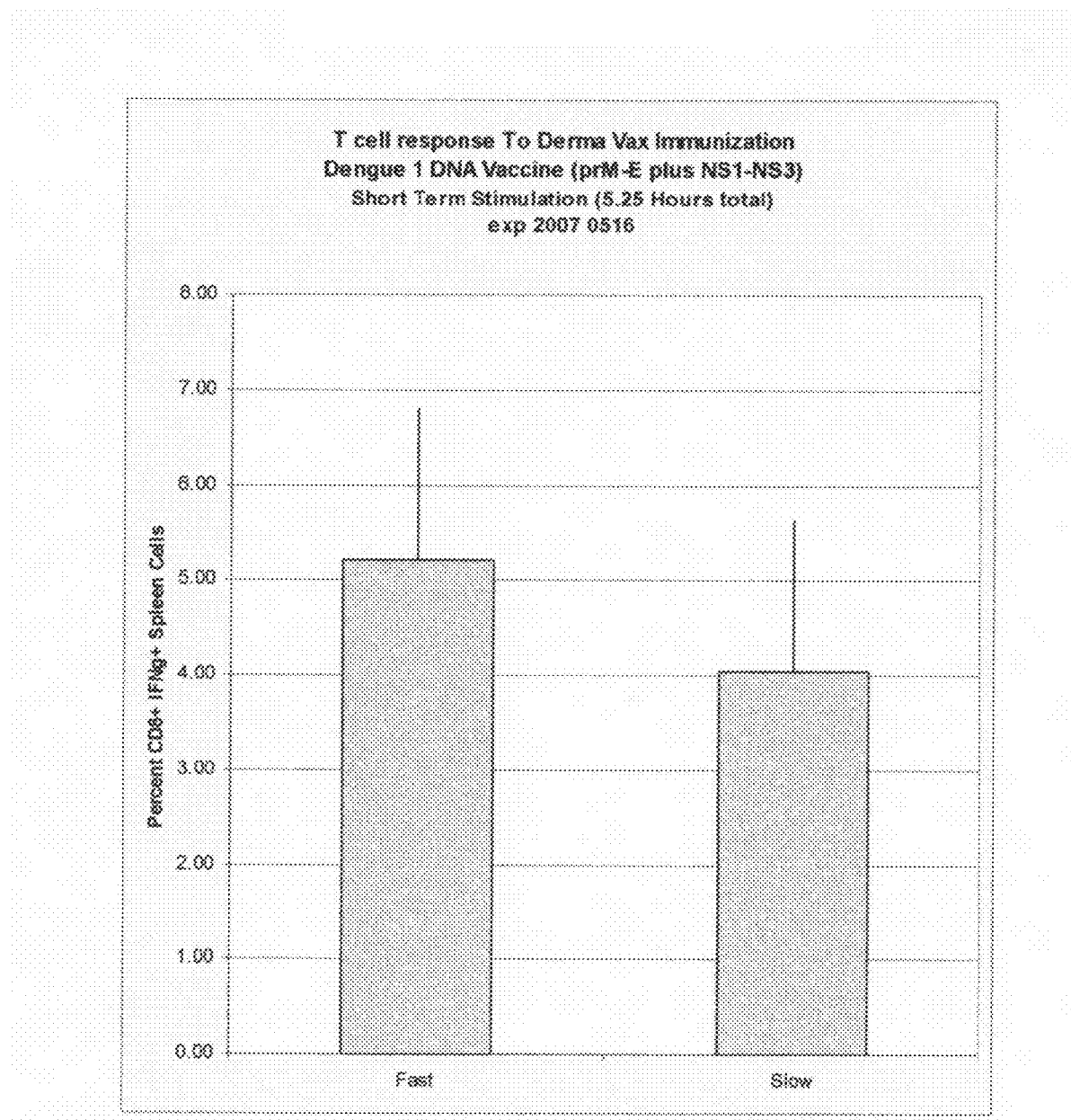
FIG. 2 a graph illustrating a comparison of T cell response to vaccination using Dengue 1 DNA vaccine, resulting from the application of fast PulseAgile electrical waveforms versus the application of slow PulseAgile electrical waveforms for delivery of the vaccine with electroporation using "Derma Vax" equipment.

Reference is made to FIG. 2 in the drawings for a graphical representation of the test results. In this respect, by conducting a Student's T test, the test results show a statistically insignificant difference between fast and slow electrical waveform protocols. In this respect, there is a statistical equivalence of T cell enhancement between fast and slow electrical waveform protocols.

CONCLUSIONS

T cell responses induced by fast PulseAgile electrical waveforms with the "Derma Vax" system are equivalent to those induced by slow PulseAgile electrical waveforms with the "Derma Vax" system with in vivo electroporation.

TABLE I

Perceptible muscle contractions are reduced by electroporation using fast PulseAgile electrical waveforms in contrast with slow PulseAgile electrical waveforms.

| Parameter | Fast Pulse Agile | Slow Pulse Agile |
|-----------|------------------|------------------|
| Pulses Delivered | 10 | 10 |
| Total Delivery Time | 0.23 Seconds | 3.5 Seconds |
| Perceptible Muscle Contractions | 1 | 10 |

Clearly, with fast PulseAgile electrical waveforms (as compared with slow PulseAgile electrical waveforms), delivery time is much less than 3.5 seconds, and only 1 muscle contraction is perceived, even when 10 pulses are delivered.

Figure 3:
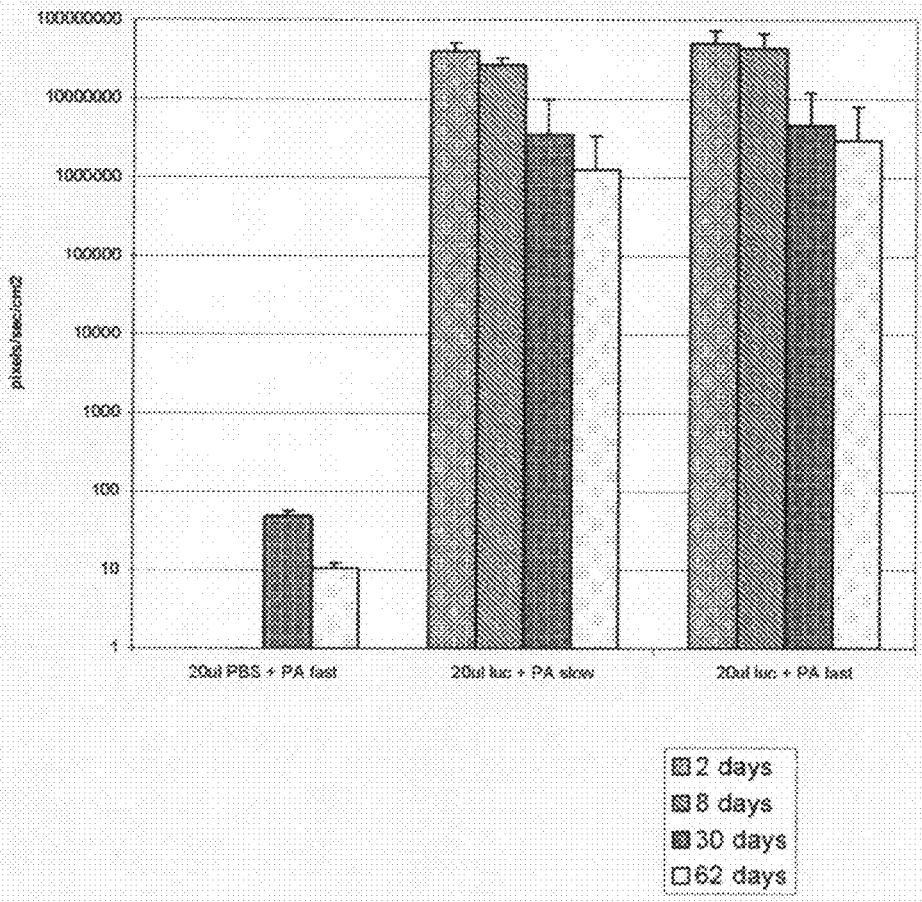
FIG. 3 is a graph illustrating a comparison of luciferase expression resulting from the application of fast PulseAgile electrical waveforms versus the application of slow PulseAgile electrical waveforms for delivery of luciferase plasmid with electroporation using "Derma Vax" equipment.

With respect to FIG. 3, DNA delivery (DNA being a polynucleotide) was carried out as follows.

Mice were anesthetized with 4% isoflurane (Baxter Medical AB, Kista, Sweden) and maintained at 2-2.5% isoflurane in a mask during immunizations. 20 μg DNA in PBS was injected intradermally on each flank, near the base of the tail, using a 29 G insulin grade syringe (Micro-Fine U-100, BD Consumer Healthcare, Franklin Lakes, N.J.).

Subsequently, a needle array electrode was placed over the raised skin area of injection and voltage was applied (2 pulses, 1125 V/cm, 50 μsec+8 pulses, 275 V/cm, 10 msec). Pulse intervals were varied to make fast and slow PulseAgile protocols.

The needle array electrode used was the Cyto Pulse Intradermal array (four needle, 4 mm gap, two rows) (Cyto Pulse Sciences, Inc. Glen Burnie, Md.). Electroporation was performed using the Derma Vax Electroporation System (Cyto Pulse Sciences, Inc.).

It is apparent from the above that the present invention accomplishes all of the objects set forth by providing a new and improved method and apparatus for the delivery of polynucleotide vaccines into mammalian skin cells that may advantageously be used and which takes less than 3.5 seconds to administer the polynucleotide vaccine. With the invention, a method and apparatus for the delivery of polynucleotide vaccines into mammalian skin cells are provided which applies plural PulseAgile electrical waveforms to the mammalian skin and only causes one muscle contraction for the plural applied electrical waveforms. With the invention, a method and apparatus for the delivery of polynucleotide vaccines into mammalian skin cells are provided which gives evidence of successful genetic expression of the administered polynucleotide vaccine. With the invention, a method and apparatus for the delivery of polynucleotide vaccines into mammalian skin cells are provided which give evidence of providing a desired protein which results from the successful genetic expression of the polynucleotide vaccine.

As to the manner of usage and operation of the instant invention, the same is apparent from the above disclosure, and accordingly, no further discussion relative to the manner of usage and operation need be provided.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

What is claimed is:

1. A method for the delivery of polynucleotide vaccines into mammalian skin cells, comprising the steps of:
   (a.) administering a polynucleotide vaccine into skin at an administration site,
   (b.) applying a needle electrode to skin in vicinity to the administration site,
   (c.) applying a sequence of at least three single, operator-controlled, independently programmed, narrow interval electrical waveforms, which have pulse intervals that are less than 100 milliseconds, to deliver the polynucleotide vaccine into the skin cells by electroporation,
   wherein the sequence of at least three waveforms has one, two, or three of the following characteristics: (1) at least two of the at least three waveforms differ from each other in waveform amplitude; (2) at least two of the at least three waveforms differ from each other in waveform width; and (3) a first waveform interval for a first set of two of the at least three waveforms is different from a second waveform interval for a second set of two of the at least three waveforms,
   whereby, by carrying out steps (a), (b), and (c) hereinabove, the administration of the polynucleotide vaccine causes only one perceived muscle contraction for the sequence of applied narrow interval electrical waveforms.

2. The method of claim 1 wherein step (a.) and step (b.) are carried out sequentially.

3. The method of claim 1 wherein step (a.) and step (b.) are carried out simultaneously using a needle electrode that is pre-coated with the polynucleotide vaccine.

4. The method of claim 1 whereby genetic expression of the administered polynucleotide vaccine is equivalent to genetic expression from applying a sequence of at least three single, operator-controlled, independently programmed, wide interval electrical waveforms, which have pulse intervals that are equal to or greater than 100 milliseconds.

5. The method of claim 1 wherein ten narrow interval electrical waveforms are applied.

6. The method of claim 5 wherein it takes approximately 0.23 seconds to administer the polynucleotide vaccine.

7. The method of claim 1, further including the step of:
   (d.) providing evidence of successful genetic expression of the administered polynucleotide vaccine.

8. The method of claim 7 wherein the evidence of successful genetic expression of the polynucleotide vaccine is provided by detection of a genetic marker in the polynucleotide vaccine.

9. The method of claim 8 wherein the genetic marker expresses luciferase protein.

10. The method of claim 7 wherein evidence of successful genetic expression of the administered polynucleotide vaccine includes providing a desired protein which results from the successful genetic expression of the polynucleotide vaccine.

11. The method of claim 10 wherein the desired protein stimulates T cell response.

12. A method for the delivery of polynucleotide vaccines into mammalian skin cells, comprising the steps of:
   (a.) administering a polynucleotide vaccine into skin at an administration site,
   (b.) applying a needle electrode to skin in vicinity to the administration site,
   (c.) applying a sequence of narrow interval electrical waveforms, which have pulse intervals that are less than 100 milliseconds, to deliver the polynucleotide vaccine into the skin cells by electroporation,
   whereby, by carrying out steps (a), (b), and (c) hereinabove, the administration of the polynucleotide vaccine causes only one perceived muscle contraction for the sequence of applied narrow interval electrical waveforms.

13. A method for the delivery of polynucleotide vaccines into mammalian skin cells, comprising the steps of:
   (a.) administering a polynucleotide vaccine into skin at an administration site,
   (b.) applying a needle electrode to skin in vicinity to the administration site, and
   (c.) applying a sequence of at least three single, operator-controlled, independently programmed, narrow interval electrical waveforms, which have pulse intervals that are less than 100 milliseconds, to deliver the polynucleotide vaccine into the skin cells by electroporation, wherein the sequence of at least three waveforms has one, two, or three of the following characteristics: (1) at least two of the at least three waveforms differ from each other in waveform amplitude; (2) at least two of the at least three waveforms differ from each other in waveform width; and (3) a first waveform interval for a first set of two of the at least three waveforms is different from a second waveform interval for a second set of two of the at least three waveforms,
   whereby, by carrying out steps (a), (b), and (c) hereinabove, the administration of the polynucleotide vaccine causes only one perceived muscle contraction for the sequence of applied narrow interval electrical waveforms, and
   whereby, by carrying out steps (a), (b), and (c) hereinabove, genetic expression of the administered polynucleotide from applying a sequence of at least three single, operator-controlled, independently programmed, narrow interval electrical waveforms, which have pulse intervals that are less than 100 milliseconds, is equivalent to genetic expression from prior art of applying a sequence of at least three single, operator-controlled, independently programmed, wide interval electrical waveforms, which have pulse intervals that are equal to or greater than 100 milliseconds.

* * * * *